United States Patent [19]

Gion et al.

[11] Patent Number: 4,641,249

[45] Date of Patent: Feb. 3, 1987

[54] METHOD AND DEVICE FOR COMPENSATING TEMPERATURE-DEPENDENT CHARACTERISTIC CHANGES IN ION-SENSITIVE FET TRANSDUCER

[75] Inventors: Hidenori Gion; Kenji Kubota, both of Okayama; Michihiro Nakamura, Soja; Makoto Yano, Kurashiki, all of Japan

[73] Assignee: Kuraray Co., Ltd., Okayama, Japan

[21] Appl. No.: 622,250

[22] Filed: Jun. 19, 1984

[30] Foreign Application Priority Data

Jun. 22, 1983 [JP] Japan ................................ 58-113298
Apr. 24, 1984 [JP] Japan .................................. 59-82698

[51] Int. Cl.[4] ..................... G01N 27/14; G01N 27/46; G06F 15/42
[52] U.S. Cl. .................... 364/496; 204/408; 204/416; 324/438; 364/550; 364/571
[58] Field of Search ............... 364/496, 497, 571, 550; 204/406, 408, 412, 416; 357/25; 324/438, 425, 459; 128/635

[56] References Cited

U.S. PATENT DOCUMENTS

| | | | |
|---|---|---|---|
| 4,180,771 | 12/1979 | Gukel | 357/25 X |
| 4,267,504 | 5/1981 | Bergveld | 324/425 X |
| 4,269,682 | 5/1981 | Yano et al. | 204/406 X |
| 4,301,807 | 11/1981 | Mentelos | 128/635 |
| 4,321,544 | 3/1982 | Riseman | 324/438 |
| 4,385,274 | 5/1983 | Shimada et al. | 204/416 X |
| 4,411,741 | 10/1983 | Janata | 204/412 X |
| 4,490,678 | 12/1984 | Kuisl et al. | 324/438 |

FOREIGN PATENT DOCUMENTS 2035577 6/1980 United Kingdom .

Primary Examiner—Felix D. Gruber
Attorney, Agent, or Firm—Birch, Stewart, Kolasch and Birch

[57] ABSTRACT

An ion activity monitoring device is disclosed, having a semi-conductor device including an ion-sensitive field-effect transistor, for detecting the activity of ions in a liquid medium of interest, and a temperature sensor, for detecting the temperature of the liquid medium of interest, a constant current circuit for supplying a drain current of a particular value to the transistor, and a processing circuit for calculating the concentration of the ions in the liquid medium of interest. The drain current is of a value satisfying the relationship of $|Id/\beta| \leq 0.10$ volt$^2$, wherein Id represents the drain current and $\beta$ represents the channel characteristic value of the ion-sensitive field-effect transistor. A method for operating the transistor is also disclosed.

9 Claims, 5 Drawing Figures 4,641,249

METHOD AND DEVICE FOR COMPENSATING TEMPERATURE-DEPENDENT CHARACTERISTIC CHANGES IN ION-SENSITIVE FET TRANSDUCER

BACKGROUND OF THE INVENTION

The present invention generally relates to the utilization of an ion-sensitive field-effect transistor and, more particularly, to a device and a method for compensating for variations in characteristics of the ion-sensitive field-effect transducer which may result from changes in temperature.

More specifically, the present invention pertains to an ion activity monitoring device utilizing the ion-sensitive field-effect transistor for the measurement of the pH value of electrolytic fluid present, for example, in a living body and also to a method for using the ion-sensitive field-effect device.

Various types of pH measuring devices utilizing the ion-sensitive field-effect transistor, hereinafter referred to as ISFET have hitherto been well known in the art. The principle of pH measurement with these types of devices is based on the utilization of a change in gate potential of the ISFET device which results from the sensitivity thereof to the activity of H+ ions contained in the electrolytic fluid of a living body while a constant current or voltage is supplied to the source-to-drain passage of the ISFET device, with the resultant pH value being delivered from the source potential.

In these prior art measuring devices, since the ISFET device tends to be affected not only by the H+ ions in the electrolitic fluid of a living body, but also by the ambient temperature, an accurate and precise measurement of the ion activity requires compensation for the temperature-dependent changes of the characteristic of the ISFET device.

British Patent Specification No. 2,035,577, published June 18, 1980, which corresponds to U.S. Pat. No. 4,267,504 discloses a device for measuring the quantity, for example, the concentration of ions in a solution such as the electrolytic fluid of the living body which will influence the ISFET device included in the pH measuring device. According to this publication, the compensator disclosed therein is intended for use in the measuring device utilizing the ISFET device as a variable resistance and is so designed that, in order to compensate for temperature-dependent changes of the ISFET device, an auxiliary signal, having a frequency located outside the frequency range of the signal representing the quantity to be measured, can be applied to the transistor, and these two signals are then separated from one another after having been processed by the measuring device. With this compensator, since both the signals of interest, that is, the signal representing the quantity to be measured, and the auxiliary signal applied to the transistor contain a signal component affected by the ambient temperature, the processing of these signals through the measuring circuit theoretically results in an output from the measuring circuit which is free from the affects of the ambient temperature.

While the measuring device disclosed in the above mentioned publication is satisfactory in that any adverse influence brought about by the ambient temperature can substantially be eliminated, it has been found that the signal of interest tends to be inevitably strained considerably at the time the auxiliary signal is applied and also at the time it is separated from the auxiliary signal in the measuring circuit. Therefore, the utilization of the measuring device disclosed in the above mentioned publication brings about a drawback in that an accurate and precise measurement tends to be adversely affected.

SUMMARY OF THE INVENTION

Accordingly, the present invention has been developed with a view to substantially eliminating the disadvantages and inconveniences inherent in the prior art measuring devices and has for its essential object to provide an improved ion activity monitoring device wherein the temperature-dependent characteristic change of the ion-sensitive field-effect transistor can be compensated for to eliminate any possible influence that the ambient temperature may have on the measurment of the ion activity.

Another important object of the present invention is to provide an improved ion activity monitoring device of the type referred to above, wherein a required correction of the operation of the transistor can be easily and precisely carried out.

It is a related object of the present invention to provide a method for using the ion-sensitive field-effect transistor to avoid the temperature dependent characteristic change which will adversely affect the precise and accurate measurement of the ion activity.

BRIEF DESCRIPTION OF THE DRAWINGS

These and other objects and features of the present invention will become readily understood from the following detailed description of the preferred embodiments thereof along with reference to the accompanying drawings, in which.

DETAILED DESCRIPTION OF THE PREFERRED EMBODIMENTS

Before the description of the preferred embodiments of the present invention proceeds, it is to be noted that like parts are designated by the like reference numberals throughout the accompanying drawings.

Figure 1:
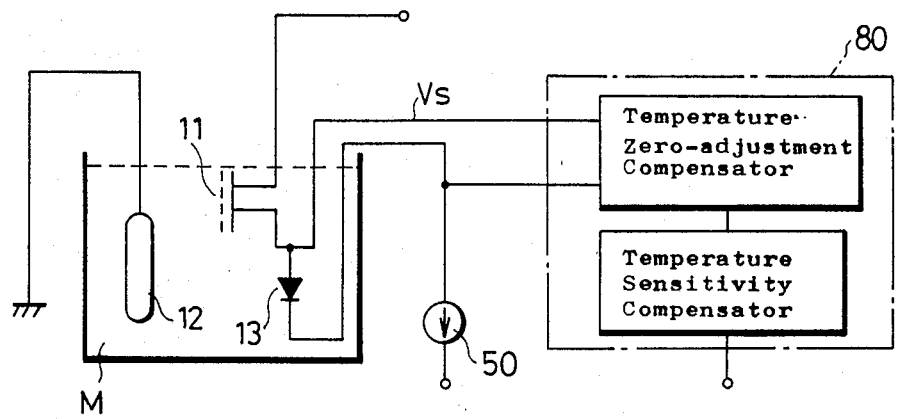
FIG. 1 is a schematic block diagram showing an ion activity monitoring device, showing the principle of the present invention.

Referring first to FIG. 1 showing the basic construction of the ion activity monitoring device according to the present invention, the circuit shown therein comprises a semi-conductor device including an ion-sensitive field-effect transistor (ISFET) 11 for detecting the activity of ions in an electrochemical solution M that is to be measured and a temperature sensor 13 for detecting the temperature of the electrochemical solution M, a constant current source 50 for supplying a predetermined value of drain current to the ion-sensitive field-effect transistor 11 so that the source potential Vs of the ion-sensitive field-effect transistor 11, which represents an output signal indicative of the activity of ions detected by the ion-sensitive field-effect transistor 11, can exhibit a linear property with respect to temperature; and a digital processor 80 adapted to receive both the output signal Vs from the ion-sensitive field-effect transistor 11 and a temperature signal D, generated from the temperature sensor 13 and indicative of the temperature of the electrochemical solution M detected thereby, and for determining the concentration of the ions contained in the electrochemical solution M.

The digital processor 80 includes a temperature compensating means for effecting a zero-adjustment in light of the temperature signal D so as to substantially eliminate the temperature dependency of the ion-sensitive field-effect transistor 11, and a sensitivity adjusting means operable in response to both of the signals Vs and D for correcting the sensitivity of the detection of the ion activity. The circuit shown in FIG. 1 also comprises a reference electrode 12 utilized to maintain the potential of the electrochemical solution M at a constant value.

The principle of the measuring method according to the present invention will now be described wherein the ion-sensitive field-effect transistor is used to detect the pH value of the solution of interest, that is, the electrochemical solution.

Referring to the circuit shown in FIG. 1, if the pH measurement carried out with the constant drain current supplied to the ion-sensitive field-effect transistor results in the source potential Vsoo indicating the reference pH value of (pH)o at a reference temperature To, the source potential Vso indicating the reference pH value of (pH)o at a measured temperature T, and the source potential Vs indicating the measured pH value of (pH) at the measured temperature T, the difference between the source potentials Vsoo and Vso is a function of temperature since the ion-sensitive field-effect transistor tends to be affected by changes in temperature:

$$dVso = Vso - Vsoo = f(T) \qquad (1)$$

The difference between the source potentials Vs and Vso is known to be proportional to the difference between the pH values (pH) and (pH)o. That is:

$$dVs = Vs - Vso = K\{(pH) - (pH)o\} \qquad (2)$$

wherein K represents a proportionality constant.

From the equations (1) and (2) above, it will readily be seen that the following equation can be obtained:

$$Vs = K\{(pH) - (pH)o\} + f(T) + Vsoo \qquad (3)$$

The proportionality constant K represents the sensitivity to the pH value of the solution of interest and is known as proportional to the absolute temperature T. That is, if $dT = T - To$, $$K = Ko(T/To) = Ko(1 + dT/To) \qquad (4)$$

wherein Ko represents the sensitivity to the pH value at the reference temperature To. If the requirements of the zero adjustment necessary to establish the following relationship were found;

$$f(T) = A \times dT \qquad (5)$$

wherein A represents a constant, the following equation (6) can be obtained by incorporating the equations (4) and (5) into the equation (3):

$$Vs = Ko(1 + dT/To)\{(pH) - (pH)o\} + A \times dT + Vsoo \qquad (6)$$

Modifying this equation (6) results in:

$$(pH) = \frac{Vs - Vsoo - A \times dT}{Ko(1 + dT/To)} + (pH)o \qquad (7)$$

The multiplication $A \times dT$ and the fraction $dT/To$ in the equation (7) above are related to the zero adjustment of Vso and the temperature compensation of the sensitivity, respectively. Since both of these temperature compensations are a linear equation of the temperature difference dT, an automatic compensation can readily be achieved by the use of an electric circuit arrangement.

The inventors of the present invention have carried out a series of experiments to find the conditions in which the ion-sensitive field-effect transistor satisfies the equation (5) above, that is, the conditions in which the source potential given at a constant pH value of the solution of interest varies proportionally with a change in temperature. As a result thereof, it has been found that the equation (5) above can be established when the drain current Id to be supplied to the ion-sensitive field-effect transistor is reduced to permit the ion-sensitive field-effect transistor to operate at a voltage within the range of $|Id/\beta| \leq 0.10$ volt$^2$, wherein $\beta$ represents the channel characteristic value of the ion-sensitive field-effect transistor as expressed by the following equation:

$$\beta = (\mu \cdot e \cdot W)/(B \cdot L) \qquad (8)$$

wherein $\mu$ represents the mobility of electrons and holes, e represents the dielectric constant, W represents the channel width, L represents the channel length, and B represents the thickness of the gate insulating layer of the ion-sensitive field-effect transistor.

Figure 2:
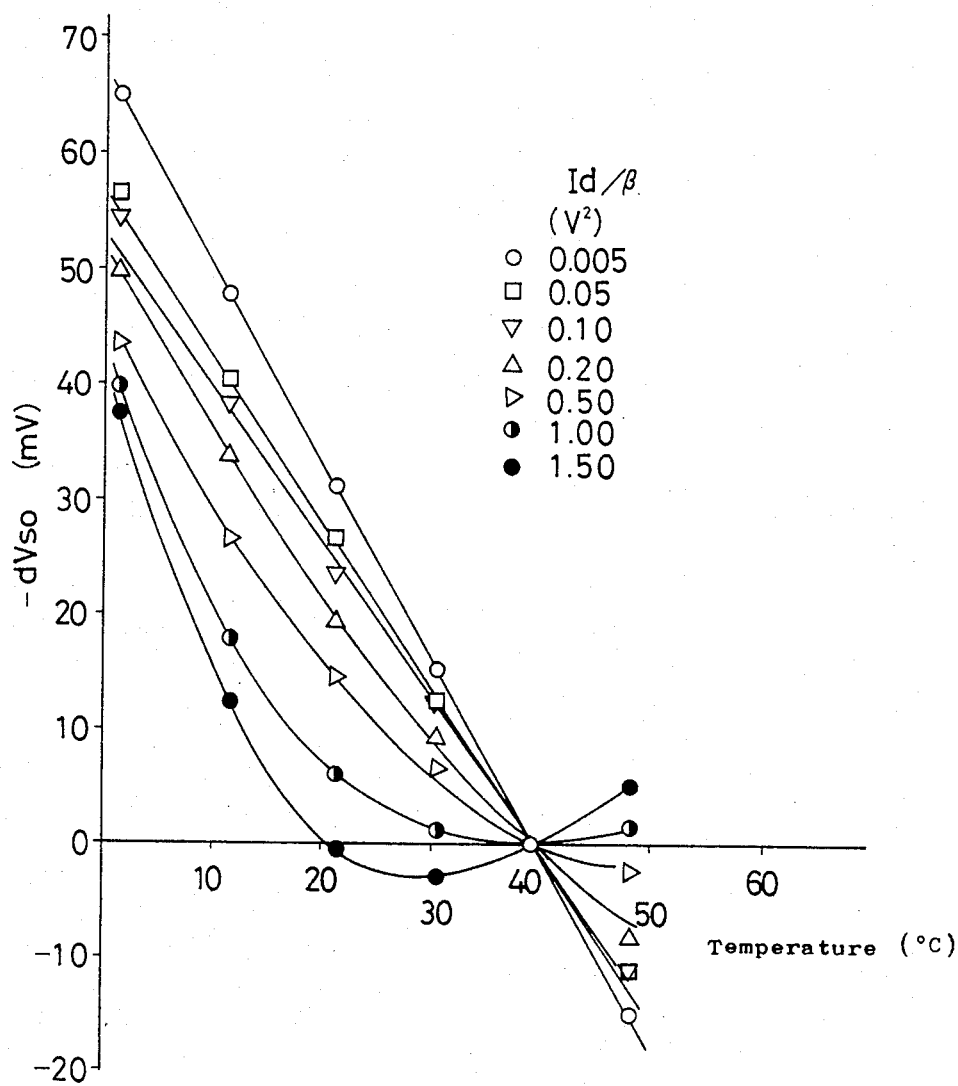
FIG. 2 is a graph showing the operating characteristics of an ion-sensitive field-effect transistor employed in the monitoring device of the present invention.

In order to find the above described range of the operating voltage for the ion-sensitive field-effect transistor, the inventors of the present invention have further conducted a series of experiments to determine how the relationship between the source potential Vso and the temperature difference dT for the reference pH value varies with the drain current Id, the results of which are plotted in the graph of FIG. 2. During the experiment, the reference temperature To and the reference pH value had been set to 313° K. (40° C.) and 6.84, respectively. In other words, the experiment was conducted in such a manner that, while the reference pH value and the source potential at 313° K. were fixed at 6.84 and a value Vsoo, respectively, the source potential Vso was measured by varying the temperature. In the graph of FIG. 2, the abscissa represents the measured temperature and the ordinate axis represents $-dVso = -Vso + Vsoo$.

As can be readily understood from the graph of FIG. 2, dVso exhibits a linear property when the absolute value $|Id/\beta|$ is equal to or lower than 0.10 volt$^2$, but dVso exhibits a non-linear property relative to the temperature when the absolute value $|Id/\beta|$ is higher than 0.10 volt$^2$. It is to be noted that, since in any customary ion-sensitive field-effect transistor, the value of $\beta$ is within the range of 200 to 1,000 $\mu$A/V$^2$, the above described linear property can be obtained when the drain current Id is equal to or lower than 20 to 200 μA, and the equation (5) described above can establish at the drain current Id within the above specified range. Accordingly, the measurement according to the present invention is carried with the use of the drain current Id that is equal to or lower than 20 to 200 μA.

Hereinafter, the ion monitoring device used to perform the measurement in the above described manner and constructed according to the present invention will be described with reference to the accompanying drawings, particularly, to FIG. 3.

Figure 3:
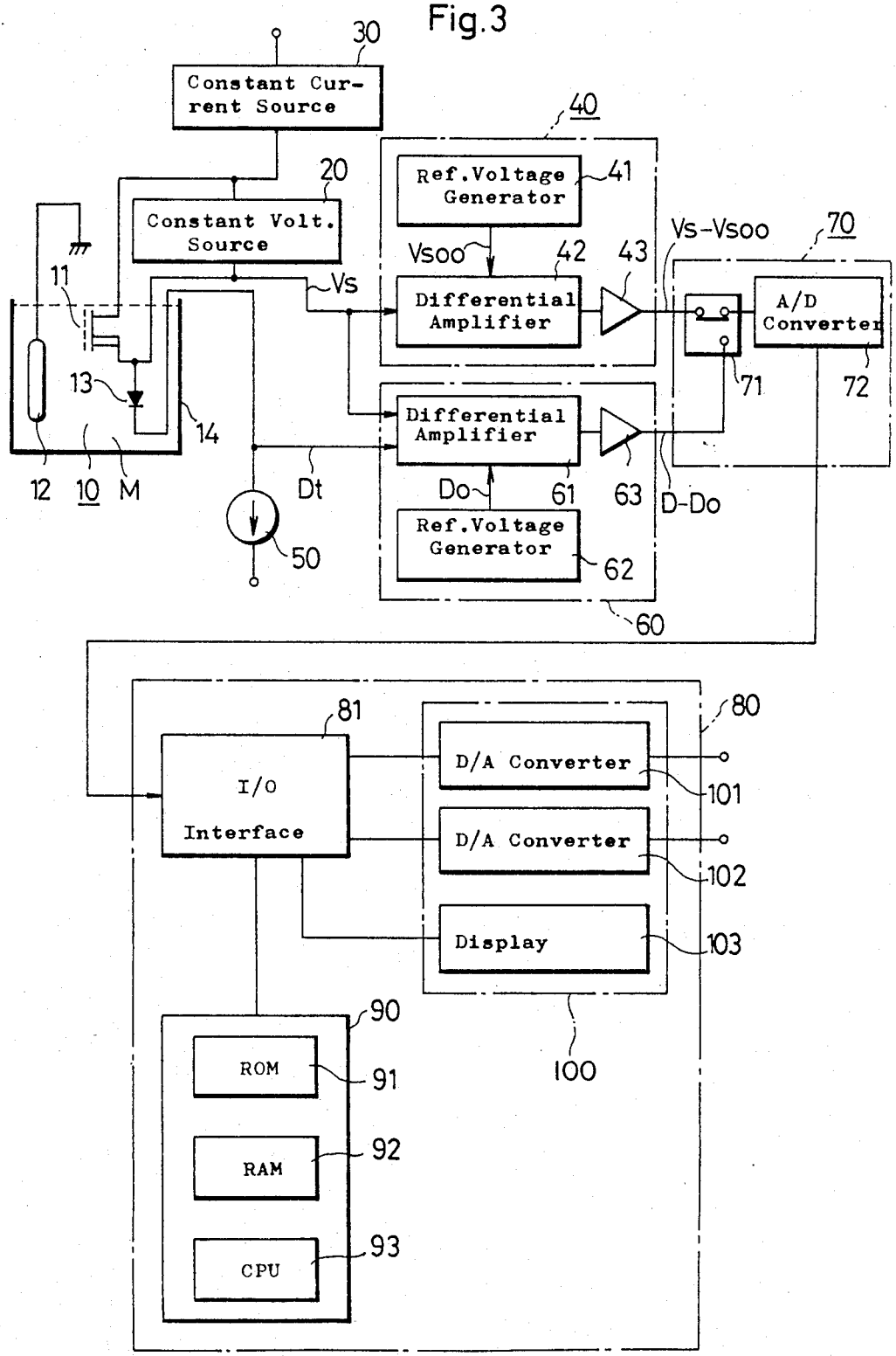
FIG. 3 is a block diagram showing the details of the ion activity monitoring device according to a preferred embodiment of the present invention.

Referring to FIG. 3, reference numeral 10 represents a sensor circuit including the ion-sensitive field-effect transistor 11, the reference electrode 12 and the temperature sensor 13 constituted by a diode. The ion-sensitive field-effect transistor 11 and the temperature sensing diode 13 are integrated together into a semi-conductor integrated circuit. Reference numeral 14 represents a vessel containing the solution M of interest which may be a body fluid of a human being.

The ion activity monitoring device according to the present invention also comprises a constant voltage source 20 inserted between the drain and the source of the field-effect transistor 11 and operable to maintain the source-to-drain voltage at a constant value regardless of the source potential Vs which may vary with the activity of ions in the solution M of interest. This constant voltage source 20 may comprise a Zener diode or the like.

The device further comprises a constant current source 30, a difference signal generator 40, the constant current circuit 50, a temperature zeroing circuit 60, an analog input device 70 and the digital processor 80, each of these circuit components being hereinafter described in details.

The constant current source 30 is operable to interrupt the supply of current to the field-effect transistor 11 and prevent the electric current from exceeding a predetermined value in the event that the drain and the source of the field-effect transistor 11 are shortcircuited with each other as a result of any possible accident. The provision of this constant current source 30 is essential particularly where the safety factor is of prime importance such as in a device for measuring the pH value of the human body fluid.

The difference signal generator 40 is constituted by a reference voltage generating circuit 41, which is a correction coefficient generating circuit for the generation of a correction coefficient used to correct the ion activity, a differential amplifier 42 and an isolation amplifier 43 for securing safety by way of insulation from the human being. This difference signal generator 40 serves to provide a difference signal representative of the difference between the source potential Vs indicating the measured pH value (pH) at the measured temperature T and the source potential Vs indicating the reference pH value (pH)o at the measured temperature To. The difference signal generator 40 is designed so as to allow the differential amplifier 42 to effect the zero adjustment by subtracting the source potential Vsoo, indicating the reference pH value (pH)o at the reference temperature To, which potential Vsoo is represented by the reference voltage fed from the generator 41, from the source potential Vs of the field-effect transistor 11 which indicates the measured pH value (pH) at the measured temperature T. The generator provides amplification by amplifying the difference to a value multiplied by tens to a few hundreds, and effects an improvement in a value corresponding to the permissible difference (some millivolts to tens millivolts) resulting from the temperature drift of the subsequent stage of the isolation amplifier 43.

The constant current circuit 50 is used to permit the activity of ions in the solution M of interest to be drawn in the form of the source potential Vs of the ion-sensitive field-effect transistor 11. This constant current circuit 50 supplies the constant current required for the drain current Id to be equal to or lower than 20 to 100 μA at which the linear property relative to the temperature can be obtained and is so selected as to permit the absolute value of Id/β to be equal to or lower than 0.10 volt$^2$ with respect to the channel characteristic value β of the field-effect transistor 11.

The temperature zeroing circuit 60 receives both the cathode potential Dt of the temperature sensing diode 13, which represents the temperature signal referred to hereinbefore, and the anode potential Vs of the temperature sensing diode 13 which represents the source potential of the field-effect transistor 11 and includes a differential amplifier 61, a reference voltage generator 62, which is a correction coefficient generator, and an isolation amplifier 63 for securing safety by way of isolation from the human being. The differential amplifier 61 serves to subtract the forward potential $D = Vs - Dt$ of the temperature sensing diode 13 given at the measured temperature T from the forward potential Do given at the reference temperature To and represented by the output from the reference voltage generator 62, and amplifies the difference 50 to 60 times, the amplified value being then applied to the subsequent stage of the isolation amplifier 63 to remove the temperature drift of the isolation amplifier 63.

The analog input device 70 includes a multiplexer 71 and an analog-digital converter 72. The multiplexer 71 serves to selectively connect one of the analog outputs from the respective isolation amplifiers 43 and 63 to the analog-to-digital converter 72. The output from the isolation amplifier 43 represents the difference of Vs−Vsoo while the output from the isolation amplifier 63 represents the difference of D−Do, and the analog-to-digital converter 72 serves to convert these analog outputs into respective digital signals one at a time depending on the position of the multiplexer 71.

The digital processor 80 operates to calculate the activity of ions in the solution of interest and has the temperature compensating means and the sensitivity adjusting means of FIG. 1, built therein. This digital processor 80 may be constituted by, for example, any known microprocessor and includes, as best shown in FIG. 3, an input/output interface 81, an arithmetic circuit 90 and an output unit 100. The input/output interface 81 has a function of controlling the input from the analog-to-digital converter 72 to the processor 80 and/or the data output to a recorder, and/or a display unit.

The arithmetic circuit 90 is constituted by a read-only memory (ROM) 91 having a predetermined program stored therein, a random access memory (RAM) 92 for storing data, and a central processing unit (CPU) 93 capable of performing various calculations. The central processing unit 93 employed in the present invention is capable of automatically calculating constants peculiar to the sensor, (such as DK, A and Ko) during the correction as will be described later and can also of calculate the ion concentration and the temperature by the use of the constants peculiar to the sensor during the measurement, an output from said central processing unit 93 being subsequently fed to one or both of a recorder and a display unit.

The output unit 100 includes a digital-to-analog converter 101 for converting the digital signal indicative of the ion activity into an analog signal, and a digital-to-analog converter 102 for converting the digital signal indicative of the temperature into an analog signal, and a display unit 103 such as, for example, a cathode ray tube or a liquid crystal display, for displaying data.

The ion activity monitoring device of the construction as hereinbefore described operates in the following manner. In this connection, the manner in which the source potential Vs indicative of the activity of ions in the solution of interest, which has been generated from the ion-sensitive field-effect transistor 11, is processed by the device to the signal indicative of the pH value of the solution of interest expressed by the equation (7) will be illustrated.

Referring to the equation (7), if dT is expressed in terms of the cathode potential (temperature signal) D of the temperature sensing diode 13, the following equation can be obtained:

$$dT = T - T_o = DK(D - D_o) \quad (9)$$

wherein DK represents a temperature coefficient of the temperature sensing diode 13 shown in FIG. 1.

By incorporating the equation (9) above into the equation (7), the following equation can be obtained:

$$(pH) = \frac{(V_s - V_{soo}) - A \times DK(D - D_o)}{K_o(1 + DK(D - D_o)/T_o)} + (pH)_o \quad (10)$$

The digital processor 80 performs a calculation in accordance with the equation (10) above with the use of the difference signal indicative of $V_s - V_{soo}$, the difference signal indicative of $D - D_o$, and the constants DK, A and Ko peculiar to the sensor to find the pH value of (pH).

Figure 4:
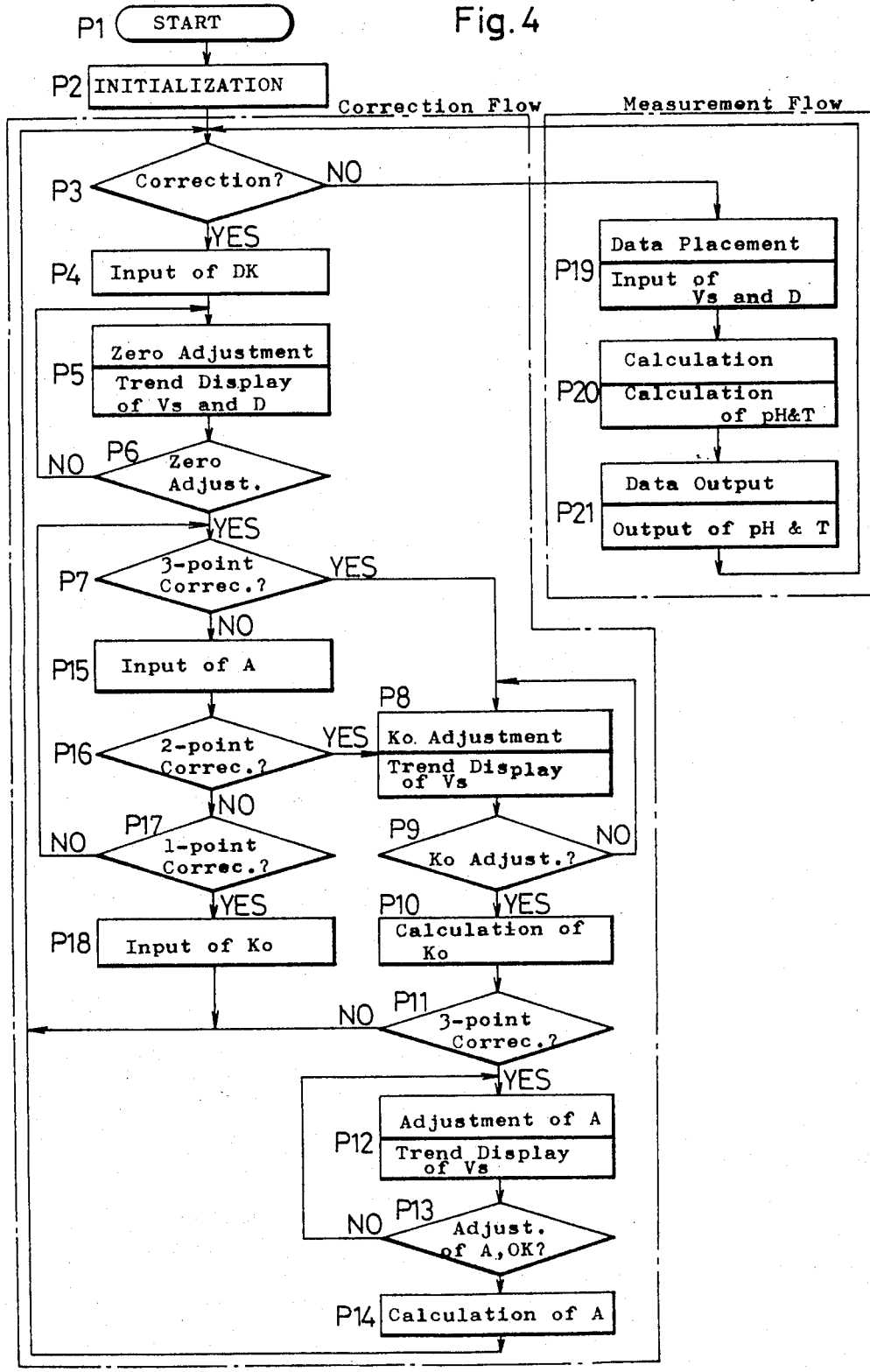
FIG. 4 is a flow chart showing the sequence of operation of a microcomputer employed in the monitoring device shown in FIG. 3.

FIG. 4 illustrates a flow chart showing the sequence of operation of the digital processor 80, reference to which will now be made. It is to be noted that the flow chart includes a correction flow used to determine the constants peculiar to each sensor before the start of measurement, and a measurement flow. The correction flow will first be described.

The method of correction includes a one-point correction method in which only the zero adjustment is carried out subject to the signals Vs and D, a two-point correction method in which both the zero adjustment of the signals Vs and D and the adjustment of the pH sensitivity Ko are carried out, and a three-point correction method in which the zero adjustment of the signals Vs and D, the adjustment of the pH sensitivity Ko and the adjustment of the temperature constant A are carried out. However, it is assumed that the correction of DK for each sensor will not be performed and the temperature coefficient DK is given a fixed value.

Referring now to the flow chart of FIG. 4, the program flow starts at the stage P1 and, at the subsequent stage P2, input and output are initialized. At the stage P3 following the stage P2, a decision is made as to whether the correction flow is to be performed or whether the measurement flow is to be performed. If the determination at the decision stage P3 indicates the correction flow to be taken, the program flow proceeds to the stage P4 at which the temperature coefficient DK of the temperature sensing diode 13 is given a fixed value.

Subsequently and at the stage P5, the zero adjustment of the source potential Vs, indicative of the ion activity, and the zero adjustment of the forward potential D of the diode which indicates the temperature signal are performed. The zero adjustment of the source potential Vs can be achieved by inserting the sensor circuit 10 into a first buffer solution having a reference temperature To, for example, 37° C., and a reference pH value (pH)o, for example, 6.84, so that the digital-to-analog converter 101 can generate an output indicative of the difference $V_s - V_{soo}$, displaying the difference $V_s - V_{soo}$ while the time elapsed is monitored, and calibrating the scale to align the zero point with the display of the difference $V_s - V_{soo}$ after the display has been settled down. Similarly, the zero adjustment of the forward potential D of the temperature sensing diode 13 can be achieved by the zeroing circuit 60 in such a way as to display the output from the digital-to-analog converter 102, which is indicative of the difference $D - D_o$, and then to calibrate the scale to align the zero point with the display of the difference $D - D_o$ after the time elapsed has been monitored and the display has subsequently settled down.

It is to be noted that, since the accuracy of the measurement will be adversely affected unless both of the differences $V_s - V_{soo}$ and $D - D_o$ are exactly zeroed, a so-called trend display in which these differences are presented in the form of a curve continuously varying with time is employed at the stage P5 so that the operator of the measuring device can sight monitor the operation.

After the completion of the zero adjustment has been confirmed at stage P6, the program flow proceeds to the stage P7 at which a decision is made as to whether or not the three-point correction method is to be taken. If the determination is yes, the program flow proceeds to the stage P8 at which the sensor circuit 10 is immersed in a second buffer solution having a reference temperature To and a predetermined pH value (pH), for example, 4.0, so that the digital-to-analog converter 101 can generate an output indicative of the source potential Vs. This source potential is then displayed and, after the time elapsed has been monitored and the display has subsequently been settled down, the program flow proceeds to the stage P9 at which the source potential Vs displayed is automatically read out. At this time, since it is important to confirm whether or not the source potential Vs has been stabilized, the trend display is employed at the stage P8 as is the case with the zero adjustment at the stage P5, so that the display can be sight monitored.

At stage P10, the pH sensitivity Ko is calculated based on the reading of the source potential Vs displayed at the stage P9. This calculation is carried out according to the previously described equation (6) and, in this equation (6), since $V_{soo} = 0$, $dT = 0$, $(pH) = 4.0$, and $(pH)_o = 6.84$ so far as the example now under discussion is concerned, the reading of the source potential at the stage P9 can give an indication of the pH sensitivity Ko.

Stage P10 is followed by stage P12 through stage P11. At the stage P12, the sensor circuit 10 is immersed in a third buffer solution having a predetermined temperature T, for example, 5° C., and a predetermined pH value (pH), for example, 7.0, so that the digital-to-analog converter 101 can generate an output indicative of the source potential Vs. This source potential Vs is displayed and, after the time elapsed has been monitored and the display has subsequently been settled down, the program flow proceeds to the stage P13 at which the source potential Vs is automatically read out. Even at stage P13, the trend display is employed. At stage 14, the temperature constant A is calculated based on the reading of the source potential Vs, using the equation (6) described above, thereby completing the three-point correction method with the program flow returning back to the stage P3 in readiness for a subsequent measurement In the case of the two-point correction method, the program flow proceeds from stage P7 to stage P15 at which the temperature constant A is given a fixed value. The program flow then skips over stage P16 onto stage P8 and, thereafter, following stages P9 and P10, the pH sensitivity Ko is determined in the manner as hereinbefore described in connection with the three-point correction method. After the completion of the two-point correction method, the program flow returns back to stage P3 in readiness for the subsequent measurement.

In the case of the one-point correction method, the program flow proceeds from stage P7 to stage P15 at which the temperature constant A is given a fixed value, followed by stage P18 through stages P16 and P17. At stage P18, the pH sensitivity Ko is also given a fixed value, thereby completing the one-point correction method with the program flow consequently returning to stage P3 in readiness for the subsequent measurement.

The measurement flow shown in FIG. 4 will now be described.

The source potential Vs, indicative of the ion activity, and the forward potential D of the diode, indicative of the temperature, are subtracted in the zeroing circuits 40 and 60, respectively, by the source potential Vsoo given at the reference temperature To and the reference pH value (pH)o, and the forward potential Do of the diode given at the reference temperature To. The zeroing circuits 40 and 60 generate the respective difference signals indicative of Vs−Vsoo and D−Do which are subsequently fed through the analog input device 70 and then through the input/output interface 81 to the arithmetic circuit 90. This process takes place at the stage P19 shown in FIG. 4. At this stage P19, the constants A, Ko and DK determined during the correction flow are also taken into the arithmetic circuit 90.

At the stage P20, using the constants A, Ko and DK, a calculation based on equation (10) described hereinbefore is performed to determine the pH value. This calculation using the equation (10) is performed by the arithmetic circuit 90 shown in FIG. 3. The calculated pH value is outputted at stage P21 and is displayed together with the temperature if necessary. The output from the arithmetic circuit 90 is fed to the output unit 100 through the input/output interface 81 of the digital processor 80 and is then displayed by the diaplay unit 103 of the output unit 100.

While the ion activity monitoring device described with reference to and shown in FIGS. 1 to 4 is constructed as hereinbefore described, it has the following advantages.

(a) During the measurement of the ion concentration, the temperature depedent change of the sensitivity to the ion activity and the temperature dependent change in zero point are eliminated and, therefore, the measurement of the ion concentration in the solution of interest can be performed accurately.

(b) Since no auxiliary signal such as disclosed in British Patent Specification No. 2,035,577, referred to hereinbefore, is employed to any one of the measured signals Vs and D, there will be no possibility that the measurement accuracy will be reduced as a result of strain caused by the addition of the auxiliary signal to the measured signals Vs and D.

(c) Since the measured signals are converted into digital signals and are then processed by the digital processor 80, the constants A and Ko peculiar to each sensor can be available in the form of digital signals during the correction. Accordingly, no adjustment of potentiometers such as required where the signals are of analog character is required and, as a result thereof, the correction manipulation can readily and easily be performed.

(d) Since the digital processor 80 requires no precise coordination between the calibrated scale of the potentiometer and the constants peculiar to each sensor, the circuit can be manufactured simply and at a low manufacturing cost.

(e) Since one of the one-point, two-point and three-point correction methods can be selected during the correction at the will of the operator depending upon the required measurement accuracy, the ion activity monitoring, device according to the present invention has a relatively wide application.

(f) Since the process of determining the pH value is digitalized, a highly accurate determination is possible as compared with the analog process.

(g) Since the determination of the pH value is carried out highly accurately as hereinbefore described, the measurement is possible with the use of the drain current of about 10 $\mu$A and there will be no possibility the patient being examined will be shocked by electricity, even if the ISFET is broken during the measurement.

In the foregoing embodiment, the digital processor 80 has been described as employed. However, instead of the employment of the digital processor, an analog processing circuit may be employed, an example of which is shown in FIG. 5.

Figure 5:
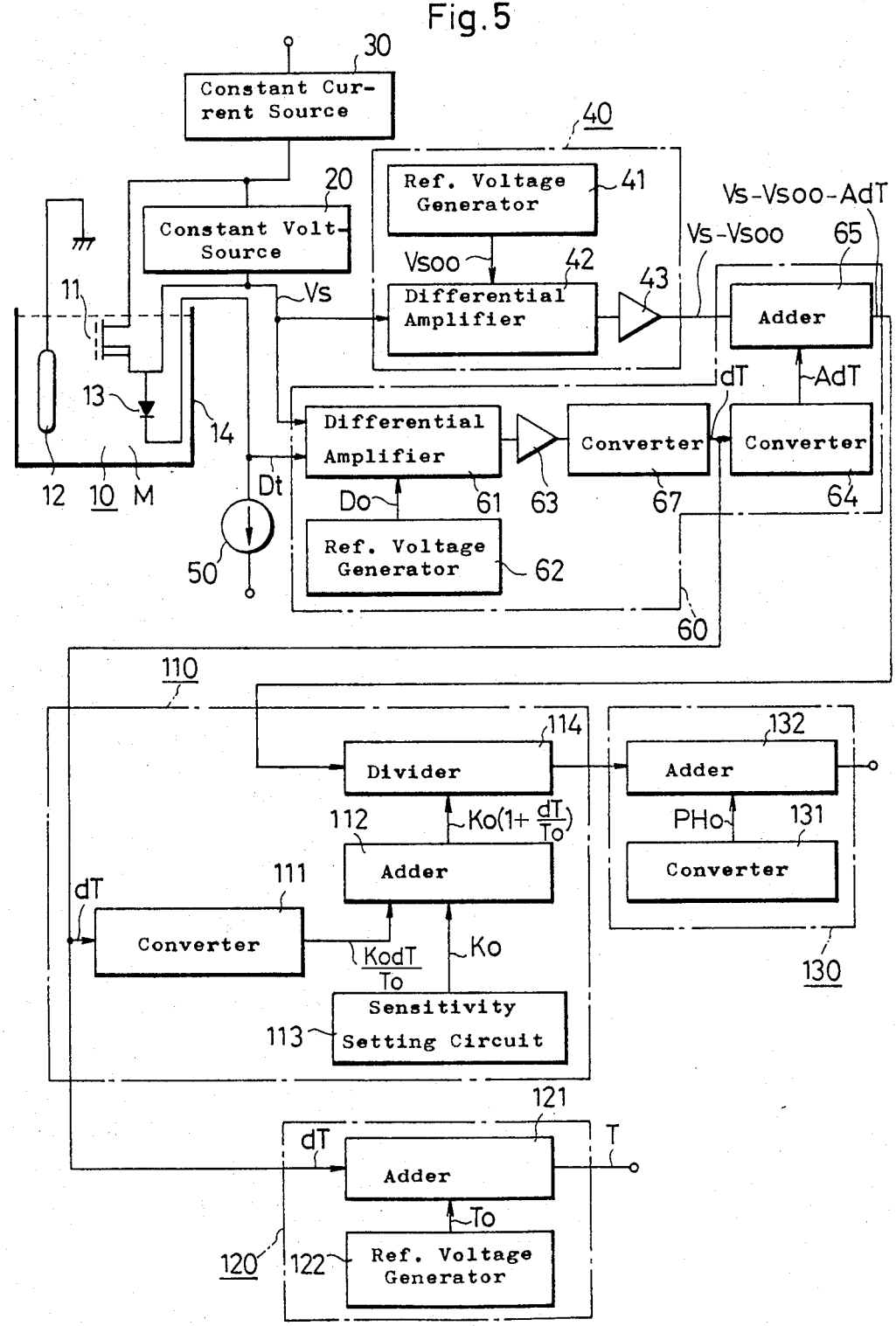
FIG. 5 is a block diagram similar to that shown in FIG. 3, showing the ion activity monitoring device according to another preferred embodiment of the present invention.

Referring now to FIG. 5, the temperature zeroing circuit 60 employed in the embodiment shown in FIG. 5 includes, in addition to the differential amplifier 61, the reference voltage generator 62 and the isolation amplifier 63, a temperature signal converter 67 for converting the output from the isolation amplifier 63 into a temperature difference signal dT, a temperature difference signal converter 64 for converting the temperature difference signal dT into a converted temperature difference signal AdT by multiplying the temperature difference signal dT by the predetermined value A, and an adder 65 adapted to receive both the converted temperature difference signal AdT from the converter 64 and the difference signal Vs−Vsoo from the isolation amplifier 43 of the zeroing circuit 40.

The output of the adder 65 is connected to a temperature-sensitivity compensating circuit 110 for compensating the temperature gradient relative to the ion activity, which circuit 110 includes a temperature-sensitivity converter 111, an adder 112, a sensor sensitivity setting circuit 113 for setting the ion sensitivity correcting coefficient Ko relative to the reference temperature To, and a divider 114.

The output of the converter 67 is connected not only to the converter 64, but also to a temperature processing circuit 120 which includes a reference voltage generator 122, that is, a temperature correction coefficient generator, for generating a reference voltage indicative of the reference temperature To, and an adder 121 for adding the reference voltage To to the temperature difference signal dT fed from the converter 67 to provide a temperature signal which is subsequently outputted from the adder 121.

The divider 114 of the compensating circuit 110 is connected to an ion concentration processing circuit 130 including an ion concentration converter 131 and an adder 132.

The ion activity monitoring device according to the embodiment shown in and described with reference to FIG. 5 operates in the following manner.

Assuming that the temperature difference signal is generated from the isolation amplifier 63 in the manner as hereinbefore described in connection with the foregoing embodiment, this temperature difference signal is then applied to the temperature signal converter 67 from which the temperature difference signal dT is generated. This temperature difference signal dT is subsequently multiplied in the temperature difference signal converter 64 by the predetermined value A and is subsequently added in the adder 65 with the difference signal $Vs - Vsoo$, generated from the isolation amplifier 43 of the zeroing circuit 40 to the adder 65. In this way, the numerator $(Vs - Vsoo - A \times dT)$ in the equation (7) above can be determined.

At the same time, the temperature difference signal dT is fed to the compensating circuit 110 so that any change in sensitivity resulting from the change in ion activity with change in temperature can be compensated. In other words, the temperature difference signal dT is fed to the sensor sensitivity converter 111 of the compensating circuit 110 at which it is converted into a signal indicative of $Ko \times dT/To$ which is represented by the output from the sensitivity converter 111. This signal, indicative of $Ko \times dT/To$, is added to the sensor sensitivity Ko by the adder 112, which sensor sensitivity Ko is associated with the reference temperature To represented by the output from the sensor sensitivity setting circuit 113, thereby to complete the calculation of the denominator $(Ko \times (1 + dT/To))$ in the equation (7) above. It is to be noted that the temperature-sensitivity converter 111 and the setting of the constant Ko by the sensitivity setting circuit 113 should be associated with each other. When the numerator is divided by the denominator in the divider 114, the quotient of the division in the equation (7) can be obtained, which quotient represents the pH value. Thus, the divider 114 generates a pH signal indicative of the above described quotient which is in turn fed to the adder 132 of the ion concentration processing circuit 130 at which it is added with the reference pH value (pH)o at the reference temperature To, which reference pH value is represented by the output from the ion concentration converter 131. The output from the adder 132 of the ion concentration processing circuit 130 indicates the final pH value measured of the solution of interest.

The ion activity monitoring device according to the second embodiment shown in and described with reference to FIG. 5 has, in addition to the advantages (a), (b), (e), and (g) described in connection with the foregoing embodiment, the following additional advantages.

(aa) During the zero point adjustment and the sensitivity adjustment incident to changes in ambient temperature around the sensor circuit which take place during the continuous monitoring, the temperature difference dT is obtained from a predetermined temperature, for example, 37° C., and both of the temperature-dependent changes are compensated for based on the temperature difference dT of relatively small value. Accordingly, as compared with the compensation using a value proportional to the absolute temperature of relatively large value, a highly accurate pH measurement can be carried out.

(bb) Since the gate-to-source voltage of the ion-sensitive field-effect transistor is maintained at a constant value by the provision of the constant current circuit 30, the source voltage Vs highly stabilized relative to change in ion concentration can be obtained.

(cc) The two isolation amplifiers 43 and 63 prevent an excessive current from flowing to the sensor circuit 10 in the event of damage occurring in the sensor circuit 10 and, accordingly, the device according to the present invention is suited for the measurement of the pH value of the human body fluid.

Although the present invention has fully been described in connection with the preferred embodiments thereof with reference to the accompanying drawings, it is to be noted that various changes and modifications are apparent to those skilled in the art. By way of example, while the temperature sensor 13 has been described as employed in the form of a diode, it may comprise a transistor or an avalanche injection diode. Both of these elements can also be integrated together with the ion-sensitive field-effect transistor into a semi-conductor integrated circuit using a common semi-conductor substrate. This advantageously brings about the low cost manufacture of the device.

Moreover, the present invention is not limited to the pH measurement. If the gate insulating layer of the ion-sensitive field-effect tranistor is made of a material having a selectivity to other ions, the device according to the present invention can also be used for the measurement of the immunity and the activity of ions in an enzyme.

Furthermore, while the reference electrode 12 employed in the device according to any one of the embodiments of the present invention has been shown as immersed in the solution of interest, it may be substituted by a reference electrode comprising a field-effect transistor such as disclosed in Japanese Laid-open Patent Publication No. 56-153247, published in 1981. In this known reference in which an electrode comprising the field-effect transistor is employed, it is necessary to supply to the field-effect transistor of the reference electrode a drain current satisfying the relationship of $|Idr/\beta r| \leq 0.10$ volt, wherein Idr and $\beta r$ represent the drain current to be supplied to the field-efect transistor of the reference electrode and the channel characteristic value of the field-effect transistor of the reference elctrode, respectively.

Therefore, such changes and modifications are to be construed as included within the scope of the present invention as defined by the appended claims unless they depart therefrom.

What is claimed is:

1. An ion activity monitoring device which comprises:
    a semi-conductor device including,
        an ion-sensitive field-effect transistor for detecting the activity of ions in a liquid medium of interest, and developing an ion activity signal indicative thereof, and a temperature sensor for detecting the temperature of the liquid medium of interest and developing a temperature signal indicative thereof;

a constant current circuit for supplying to the ion-sensitive field-effect transistor a drain current satisfying the following relationship;

$$|Id/\beta| \leq 0.10 \text{ volt}^2$$

wherein Id represents the drain current and $\beta$ represents the channel characteristic value of the ion-sensitive field-effect transistor during the operation thereof; and a processing circuit, responsive to both the ion activity signal from the ion-sensitive field-effect transistor and the temperature signal from the temperature sensor, for calculating the concentration of the ions in the liquid medium of interest, said processing circuit including, temperature zero-adjustment compensating means for effecting a zero adjustment to the ion activity signal from the ion-sensitive field-effect transistor, and a zero adjustment to the temperature, signal from the temperature sensor, and temperature sensitivity compensating means for adjusting the sensitivity of the monitoring device to the ion activity, based on both the ion activity signal and the temperature signal.

2. A device as claimed in claim 1, wherein said processing circuit is a digital processor.

3. A device as claimed in claim 1, wherein said processing circuit is an analog processor.

4. The device of claim 1, wherein said zero-adjustment compensating means includes:

difference signal generator means for producing a first difference signal $V_s - V_{soo}$ indicative of a difference between an electric potential, Vs, at a source of said ion-sensitive field-effect transistor, Vs being indicative of a measured pH value at a measured temperature T, and a reference electric potential, Vsoo, indicative of a reference pH value at a reference temperature To; and temperature zeroing means for producing a temperature difference signal $D - Do$, said temperature difference signal being indicative of a difference between the measured temperature T and the reference temperature To.

5. The device of claim 4 wherein said zero-adjustment compensating means further includes:

a multiplexer selectively applying either said first difference signal or said temperature difference signal to an input of an analog to digital converter, said analog to digital converter producing an output signal that is a digital representation of the selected input to the analog to digital converter.

6. The device of claim 5 wherein said temperature sensitivity compensating means includes:

digital processing means for storing a plurality of reference values and for producing a display of the ion activity of the liquid medium based on receipt of the output signal of the analog to digital converter and said plurality of reference values stored in the digitial processing means.

7. The device of claim 4 wherein said zero-adjustment compensating means further includes:

first converter means for converting said temperature difference signal $D - Do$ into a second difference signal dT;

multiplying means for multiplying said second difference signal by a predetermined temperature constant signal, A, to produce a signal AdT; and adding means for adding said first difference signal and said signal AdT to produce zero-adjustment output signal Vs−Vsoo−AdT.

8. The device of claim 7 wherein said temperature sensitivity compensating means includes;

second converter means for converting said second difference signal, dT, by multiplying dT by a sensitivity correcting coefficient signal, Ko to produce a product signal and dividing the product signal by the reference temperature signal To, thereby producing second converter means output KodT/To;

second adding means for adding said sensitivity correcting coefficient signal Ko to said second converter means output to produce a second adding means output signal Ko(1+dT/To); and dividing means for producing a temperature sensitivity compensating output signal by dividing said zero-adjustment output signal by said second adding means output signal, said temperature sensitivity compensating output signal being equal to (Vs−Vsoo−AdT)/Ko(1+dT/To).

9. The device of claim 8 wherein said processing circuit further includes:

an ion concentration processing circuit providing the concentration of ions in the liquid medium as a pH value from said temperature sensitivity compensating output signal by adding a reference pH value signal (pH)o to said temperature sensitivity compensating output signal.

* * * * *